(12) United States Patent
Lamberson et al.

(10) Patent No.: US 10,073,020 B2
(45) Date of Patent: Sep. 11, 2018

(54) MODULAR LIGHT GAS ACCELERATOR

(71) Applicants: Leslie Lamberson, Philadelphia, PA (US); Philipp Boettcher, Philadelphia, PA (US)

(72) Inventors: Leslie Lamberson, Philadelphia, PA (US); Philipp Boettcher, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 104 days.

(21) Appl. No.: 15/014,337

(22) Filed: Feb. 3, 2016

(65) Prior Publication Data

US 2016/0231217 A1   Aug. 11, 2016

Related U.S. Application Data

(60) Provisional application No. 62/112,690, filed on Feb. 6, 2015.

(51) Int. Cl.
  *F41A 1/00* (2006.01)
  *F41A 1/02* (2006.01)
  (Continued)

(52) U.S. Cl.
  CPC ............ *G01N 3/307* (2013.01); *F41A 1/00* (2013.01); *F41A 1/02* (2013.01); *F41B 11/00* (2013.01); *F41B 11/723* (2013.01); *G01N 3/30* (2013.01)

(58) Field of Classification Search
  CPC .... F41A 1/00; F41A 1/02; F41B 11/00; F41B 11/723
  See application file for complete search history.

(56) References Cited

U.S. PATENT DOCUMENTS 2,882,796 A * 4/1959 Clark .................. F41F 1/00
   42/76.01
3,148,587 A * 9/1964 Melhart ................ F41B 6/00
   124/3
(Continued)

FOREIGN PATENT DOCUMENTS

CN   102778171   11/2012
CN   203464849   3/2014
(Continued)

OTHER PUBLICATIONS

"Drexel University College of Engineering Senior Design Projects 2014", 2014.*
(Continued)

*Primary Examiner* — David A Rogers
(74) *Attorney, Agent, or Firm* — Joseph E. Maenner; Maenner & Associates, LLC

(57) ABSTRACT

A modular light gas accelerator includes a first stage having a chamber having a rear portion and a discharge portion and a barrel located inside the chamber. The barrel has a rear port at the rear portion of the chamber and a discharge port extending outwardly from the discharge portion of the chamber. A piston is slidingly located inside the barrel proximate to the rear port and is adapted to be propelled through the barrel and out of the discharge port. A second stage includes a receiver adapted to receive the piston from the discharge port. The receiver has a receiver passage. A frangible member extends across the receiver passage. A projectile is located downstream of the frangible member. The projectile is adapted to travel along the receiver passage. A target chamber is located at a downstream end of the receiver passage.

20 Claims, 13 Drawing Sheets

(51) Int. Cl.
*F41B 11/00* (2013.01)
*F41B 11/72* (2013.01)
*G01N 3/307* (2006.01)
*F41B 11/723* (2013.01)
*G01N 3/30* (2006.01)

(56) References Cited

U.S. PATENT DOCUMENTS

| | | | | |
|---|---|---|---|---|
| 3,267,720 A * | 8/1966 | Escallier | ............... | G01M 9/02 73/12.11 |
| 3,465,638 A * | 9/1969 | Canning | ............... | F41F 1/00 89/14.05 |
| 3,509,419 A * | 4/1970 | Berg | ............... | H01J 27/02 250/281 |
| 3,601,061 A * | 8/1971 | Dardick | ............... | F41A 9/27 102/434 |
| 4,658,699 A | 4/1987 | Dahm | | |
| 4,938,112 A * | 7/1990 | Hertzberg | ............... | F41A 1/02 60/768 |
| 5,016,537 A * | 5/1991 | Pinson | ............... | F41A 1/02 102/443 |
| 5,063,826 A * | 11/1991 | Bulman | ............... | F02K 7/10 102/374 |
| 5,194,690 A * | 3/1993 | Guthrie | ............... | F41A 1/00 102/307 |
| 5,239,930 A | 8/1993 | Adam et al. | | |
| 5,365,913 A | 11/1994 | Walton | | |
| 5,417,140 A * | 5/1995 | Onozuka | ............... | F41B 6/006 124/3 |
| 6,089,139 A * | 7/2000 | Russell | ............... | F41A 1/00 89/14.05 |
| 6,668,699 B2 * | 12/2003 | Russell | ............... | F41A 1/00 89/14.05 |
| 7,775,148 B1 * | 8/2010 | McDermott | ............... | F41A 1/02 124/60 |
| 7,954,413 B2 | 6/2011 | Koth | | |
| 8,201,486 B1 | 6/2012 | Fuhrman | | |
| 8,979,033 B2 * | 3/2015 | Hunter | ............... | F41A 1/02 244/158.5 |
| 9,772,157 B2 * | 9/2017 | Yoakam | ............... | F41A 21/28 |
| 9,784,523 B2 * | 10/2017 | Grace | ............... | F41B 6/003 |
| 9,862,506 B2 * | 1/2018 | Palmer | ............... | B64G 1/409 |
| 9,915,496 B2 * | 3/2018 | Bergeron | ............... | F41B 11/68 |
| 2002/0100361 A1 * | 8/2002 | Russell | ............... | F41A 1/00 89/14.5 |
| 2010/0212481 A1 * | 8/2010 | Koth | ............... | F41A 1/00 89/7 |
| 2016/0161212 A1 * | 6/2016 | Bergeron | ............... | F41B 11/68 124/73 |
| 2016/0341514 A1 * | 11/2016 | Grace | ............... | F41A 1/02 |

FOREIGN PATENT DOCUMENTS

| | | | | |
|---|---|---|---|---|
| WO | WO2011117661 | | 9/2011 | |
| WO | WO 2013041826 A1 * | | 3/2013 | ............... G21B 1/03 |

OTHER PUBLICATIONS

LinkedIn Profile for Brenden O'Brien, publication date unknown.*
"Teaching", available at <https://www.dynamic-lamberson.com/teaching>, publication date unknown.*
www.physicsapp.com/two-stage_gas_guns.html. Jan. 9, 2015. 2 pages.
Doolan, Con. "A Two-Stage Light Gas Gun for the Study of High Speed Impact in Propellants", Department of Defence, Defence Science & Technology Organisation. Jan. 2001. 30 pages.
Lamberson, Leslie, et al. "Pressure-Differential Hypervelocity Impact Range PHIR—A Novel Combustionless Two-Stage Light-Gas Gun". May 20, 2014. 83 pages.
Barber, John, et al. Senior Design Report Winter 2014—Pressure-Differential Hypervelocity Impact Range (PHIR). May 23, 2014. 72 pages.

* cited by examiner

MODULAR LIGHT GAS ACCELERATOR

CROSS-REFERENCE TO RELATED APPLICATION

The present application claims priority from U.S. Provisional Patent application Ser. No. 62/112,690, filed on Feb. 6, 2015, which is incorporated by reference herein in its entirety.

BACKGROUND OF THE INVENTION

Understanding material properties under a wide range of dynamic loading and impact conditions is critical to effectively utilize these materials for a variety of applications in shielding and collision design. Testing under uniform compression loading conditions is typically achieved by universal testing machines at strain rates of around $10^{-4}$ to $10^{-1}$ s$^{-1}$ and under dynamic uniform conditions using Kolsky (split-Hopkinson) bars at strain rates up to $10^2$ to $10^4$ s$^{-1}$. At the same time, non-uniform or impact loading tests are also critical for realistic material survivability investigations, and are often done using drop tower tests, plate impactors and using single and two-stage light gas guns.

In order to achieve the high speeds for such testing, conventional gas guns use combustible gases to provide the motive force to accelerate the object. Additionally, conventional accelerators can be expensive to operate on a "cost per shot" basis. Further, conventional accelerators tend to have significantly large footprints (typically over 20 feet in length) and are configured for a single type of operation.

It would be beneficial to provide an accelerator that does not need combustible material to generate acceleration forces, is relatively small and inexpensive to operate, and can be readily reconfigured for use in different types of accelerator applications.

BRIEF SUMMARY OF THE INVENTION

Briefly, the present invention provides a modular light gas accelerator comprising a first stage including a chamber having a rear portion and a discharge portion and a barrel located inside the chamber. The barrel has a rear port at the rear portion of the chamber and a discharge port extending outwardly from the discharge portion of the chamber. A piston is slidingly located inside the barrel proximate to the rear port and adapted to be propelled through the barrel and out of the discharge port. A second stage is removably attached to the discharge end of the first stage. The second stage includes a receiver adapted to receive the piston from the discharge port. The receiver has a receiver passage having a first upstream diameter and a second downstream diameter, smaller than the first upstream diameter. A frangible member extends across the second downstream diameter. A projectile is located downstream of the frangible member. The projectile is adapted to travel along the receiver passage. A target chamber is located at a downstream end of the receiver passage, such that a target is able to be mounted in the target chamber and be struck by the projectile after the projectile exits the receiver passage.

The present invention further provides a modular light gas accelerator comprising a launch portion comprising a compressed gas cylinder having an interior and a launch barrel located in the compressed gas cylinder. The barrel has an opening in fluid communication with the interior of the compressed gas cylinder. The opening has a length. A target portion is releasably connected to the launch portion. The target portion comprises an adapter block having an input passage end in fluid communication with the barrel, an output passage end, and a passage having a decreasing diameter between the input passage end and the output passage end, a frangible member disposed downstream of the output passage end, and a projectile disposed downstream of the frangible member.

Additionally, the present invention provides a light gas accelerator comprising a chamber having a rear portion and a discharge portion and a barrel located inside the chamber. The barrel has a rear port at the rear portion of the chamber, a discharge port extending outwardly from the discharge portion of the chamber, and an opening proximate to the discharge end and in fluid communication with the chamber. The opening has a length. A piston is slidingly located inside the barrel proximate to the rear port and adapted to be propelled through the barrel and out of the discharge port. The piston has a length longer than the length of the opening.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

DETAILED DESCRIPTION OF THE INVENTION

Figure 1:
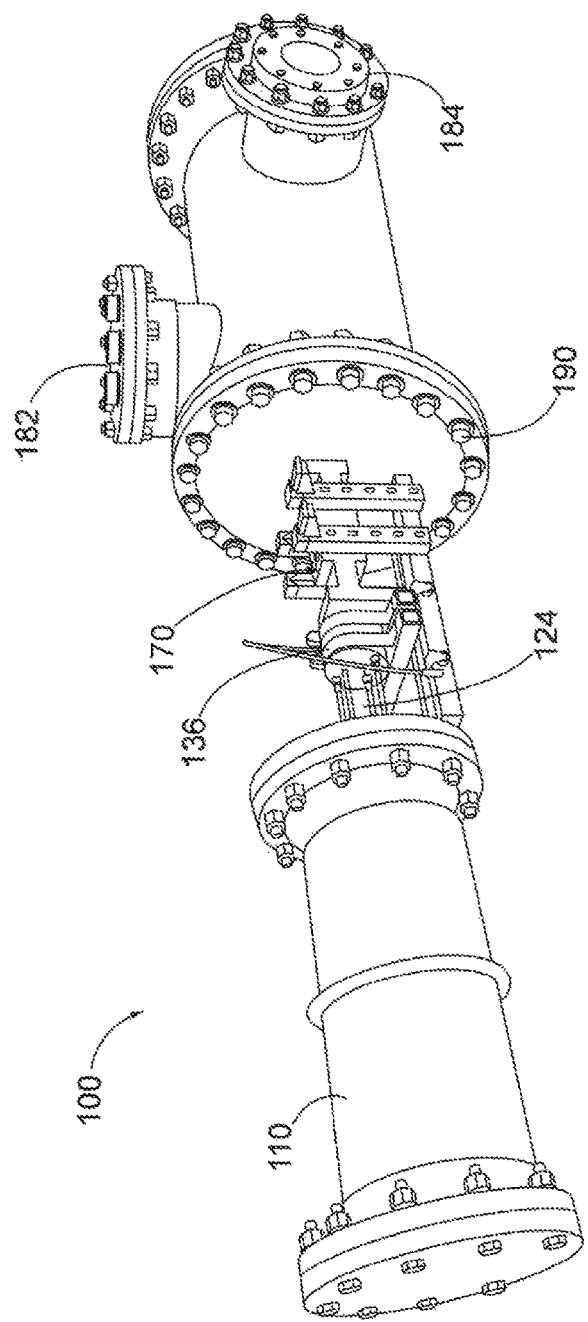
FIG. 1 shows a perspective view of a modular light gas accelerator according to an exemplary embodiment of the present invention.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "rear" is used to mean a direction upstream of operation of the inventive accelerator device, or toward the left side of FIG. 1 and the term "forward" or "discharge" is used to mean a direction downstream of operation of the inventive accelerator device, or toward the right side of FIG. 1.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments.

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements.

The modular light gas accelerator according to the present invention can be used to project small particles at high velocities using only compressed gas and without the need for dangerous explosives or combustible materials. Such inventive accelerator can be used with test materials to determine the survivability of the test materials after impact. The modular feature of the inventive light gas accelerator allows for multiple configurations of the accelerator to perform different types of testing.

Figure 1A:
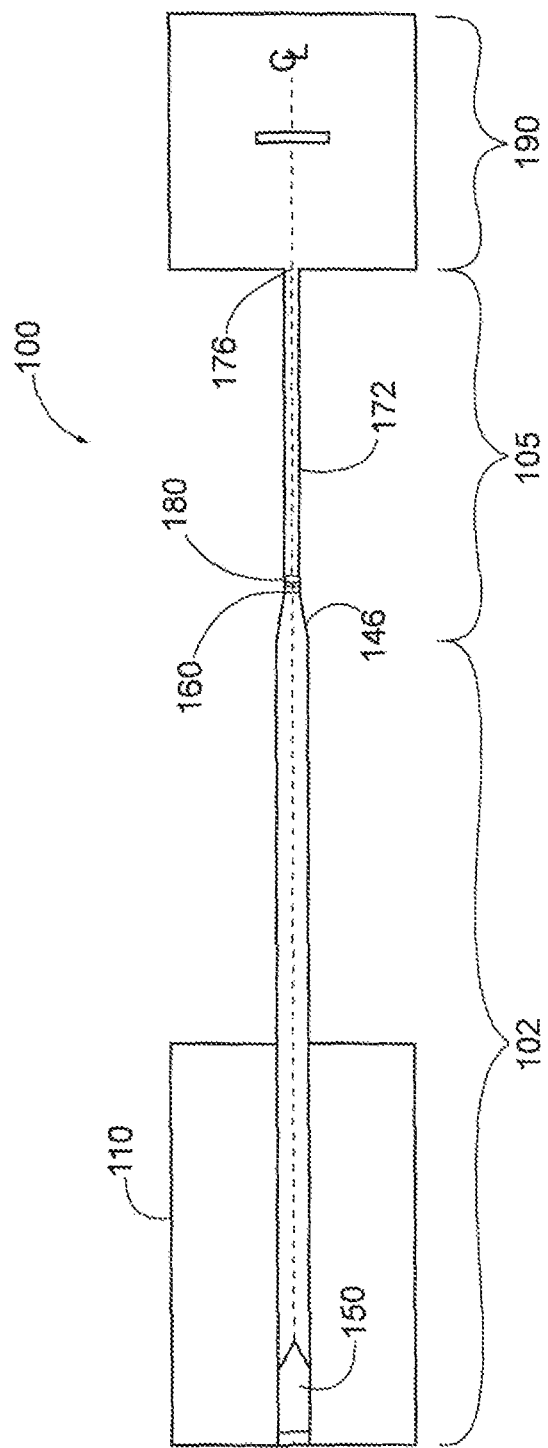
FIG. 1A shows a schematic view of the modular light gas accelerator of FIG. 1.

Referring to FIGS. 1 and 1A, a modular light gas accelerator 100 ("accelerator 100") according to an exemplary embodiment of the present invention is shown. The full configuration of accelerator 100 is shown in FIG. 1. The full configuration of accelerator 100 is a two-stage accelerator, namely, a first stage 102, which is a launch portion, and a second stage 105, which is a launch portion, and the target tank 190, which is a target portion, but it will be shown that accelerator 100 can be reconfigured into different configurations in order to be able to perform different types of impact testing.

Figure 2:
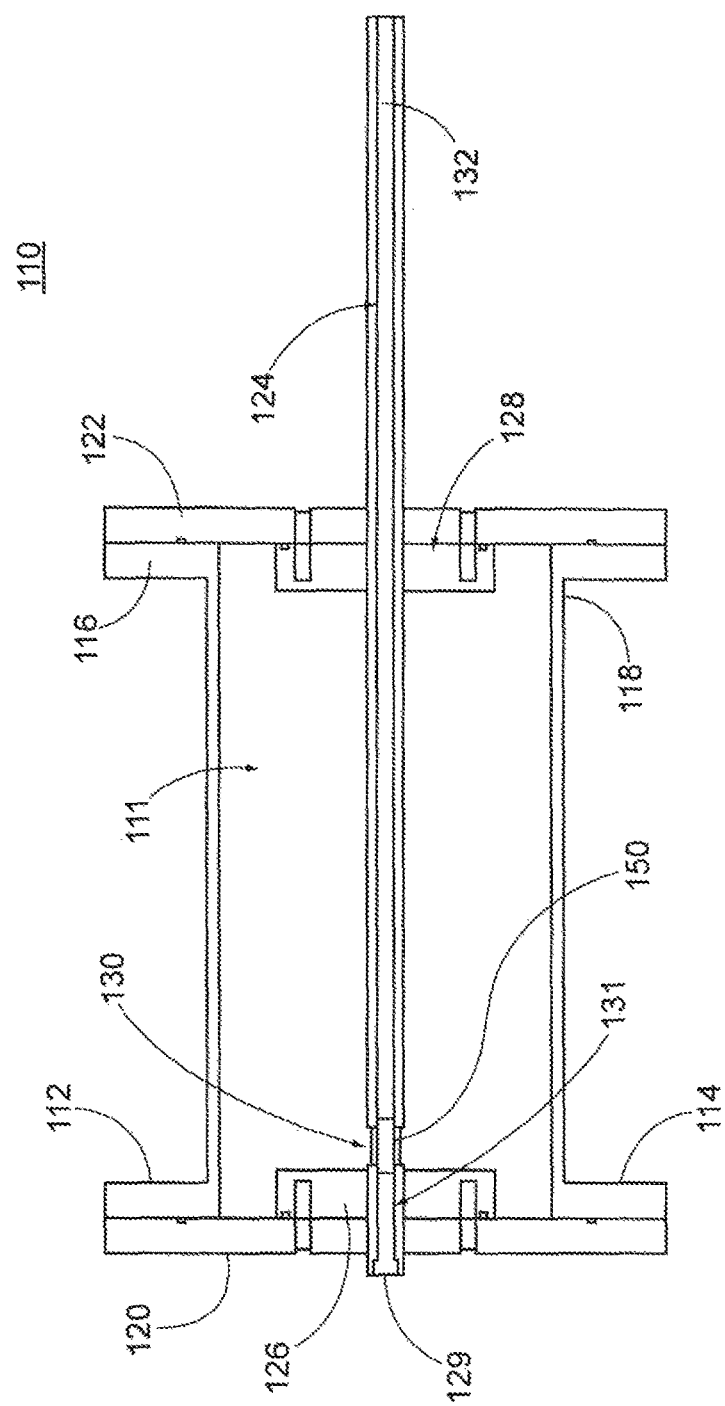
FIG. 2 shows a side elevational view, in section, of a compressed air chamber used with the gas accelerator shown in FIG. 1.

Accelerator 100 includes a compressed gas cylinder, such as an air chamber 110, the details of which are shown in FIG. 2. Compressed air chamber 110 is a generally cylindrical chamber defining a breech 111. Compressed air chamber 110 includes a rear flange 112, located at a rear portion 114 of air chamber 110 and a forward flange 116 located at a forward, or discharge, portion 118 of air chamber 110. A rear cover 120 is releasably secured to rear flange 112 and a forward cover 122 is releasably secured to forward flange 116. In an exemplary embodiment, a maximum working pressure for breech 111 can be about 400 psia using appropriately rated pressure vessel piping and flanges based on ASTM standards.

Figure 3:
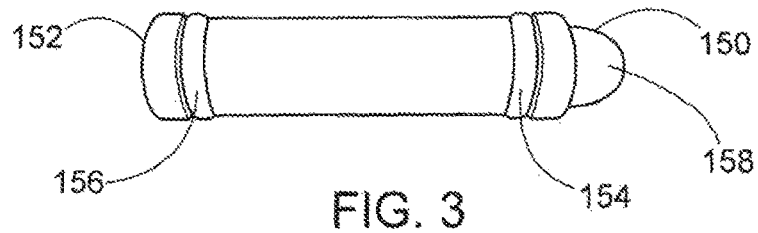
FIG. 3 shows a side elevational view of a piston used in the gas accelerator shown in FIG. 1.

A hollow barrel 124 extends from a rear of air chamber 110, through rear cover 120, extending through breech 111, and exits air chamber 110 outward beyond forward flange 116. Barrel 124 is used to accelerate a piston 150, shown in FIG. 3. A rear flange seal 126 seals barrel 124 to rear flange 112 and a forward flange seal 128 secures barrel 124 to forward flange 122.

Figure 2A:
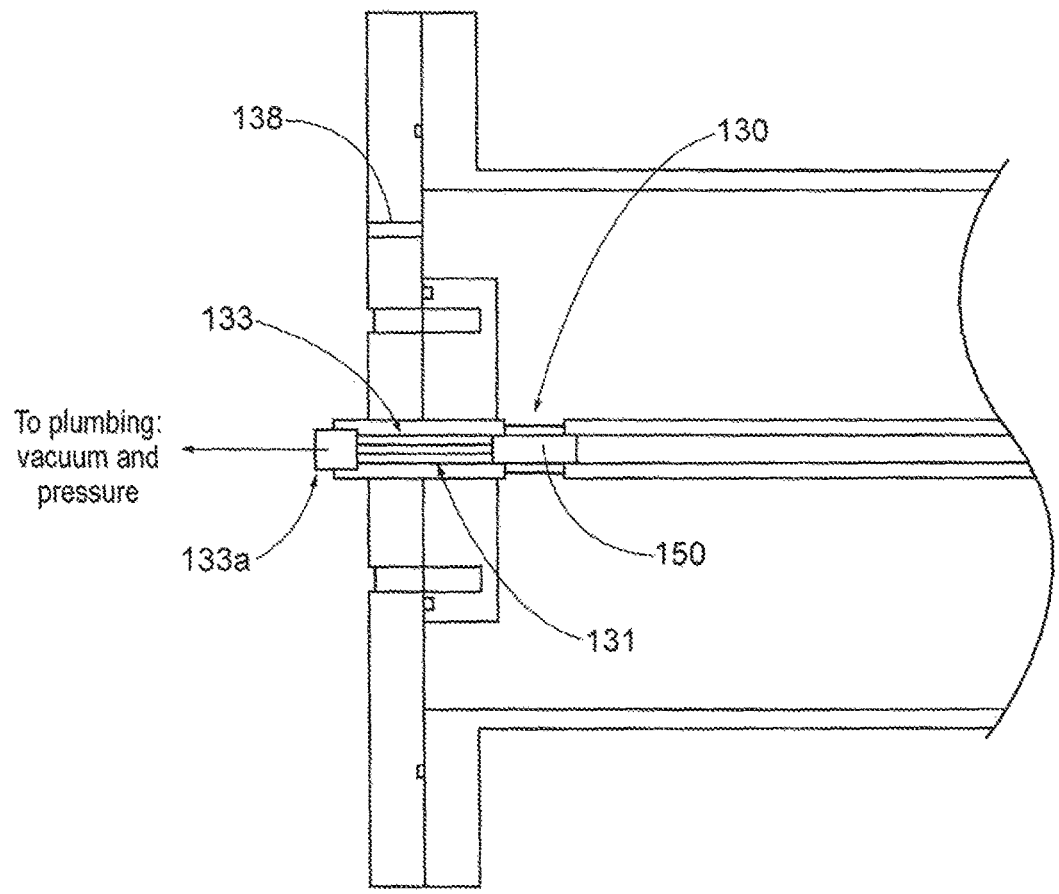
FIG. 2A shows an enlarged view of a rear portion of the barrel of the accelerator shown in FIG. 2.

Referring to FIG. 2A, barrel 124 includes a plumbing port 129 located at rear cover 120 and a pair of air slots 130 formed in the sidewalls of barrel 124, distal of rear flange seal 126, that provide fluid communication between the interior of barrel 124 and breech 111. Piston 150 is slidingly located inside barrel 124 proximate to plumbing port 129 and is adapted to be propelled through barrel 124 and out of the discharge port 132.

A vacuum hold 131 is formed inside a hollow insert spacer 133 between plumbing port 129 and piston 150. Spacer 133 provides a positive stop for piston 150 against the rear of air chamber 110. Spacer 133 is also sized to locate piston 150 along air slots 130. Air slots 130 are sized such that, in such configuration, piston 150 is sufficiently large to obscure the entire opening of air slots 130. A plug 133a in plumbing port 129 provides a connection to a vacuum line 135 and a compressed air line 137 (shown in FIG. 3A).

Piston 150 and spacer 133 are inserted into barrel 124 through plumbing port 129 prior to inserting plug 133a into plumbing port 129.

Figure 3A:
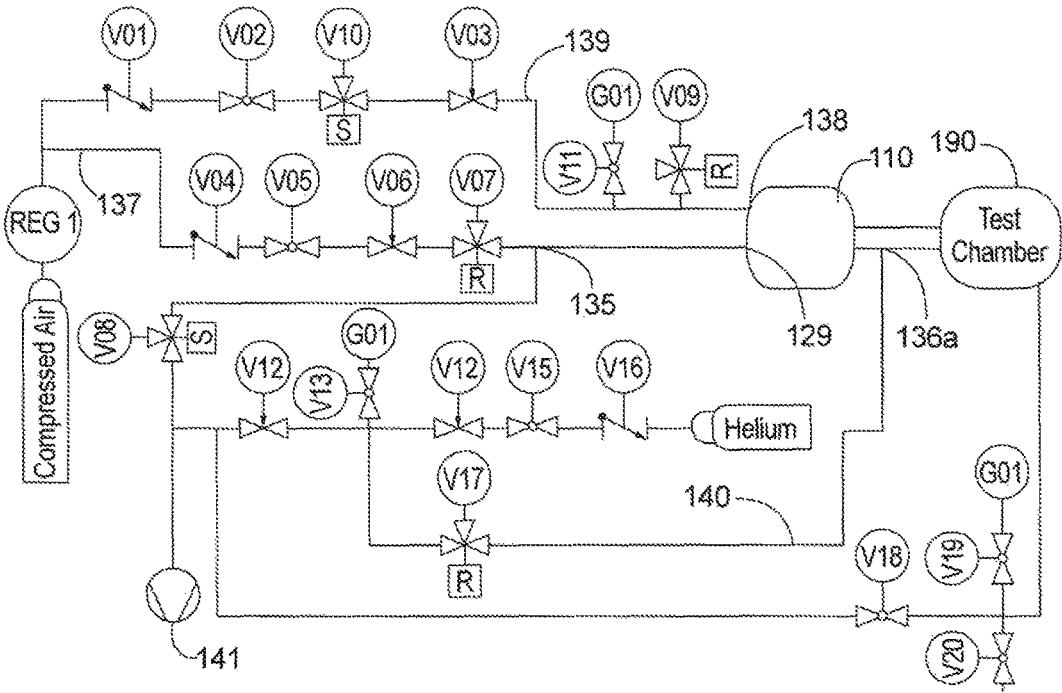
FIG. 3A shows a schematic view of an exemplary plumbing system use with the gas accelerator shown in FIG. 1.

A breech port 138 is coupled to a compressed air line 139 that provides fluid communication for gas from exterior through rear cover 120 to pressurize breech 111. In an exemplary embodiment, compressed air line 139 can be connected to the same gas supply as compressed air line 137. An exemplary plumbing diagram of accelerator 100 is shown in FIG. 3A.

The vacuum is applied to hold piston 150 in place while breech 111 is pressurized. The vacuum is applied by connecting the plug in port 129 and opening the valve connecting the system to a vacuum pump 141.

Barrel 124 further includes a discharge port 132 that discharges piston 150 forward of compressed air chamber 110 during operation. When piston 150 is ready for launch, the vacuum is secured and the compressed air is provided by compressed air line 137 to launch piston 150 through barrel 124 until piston 150 is forward of air slots 130, at which point the pressurized air in breech 111 accelerates piston 150 to discharge port 132 of barrel 124. In an exemplary embodiment, breech 111 can be pressurized to about 65 psig, which results in a launch speed of about 35 meters per second for piston 150.

Figure 4:
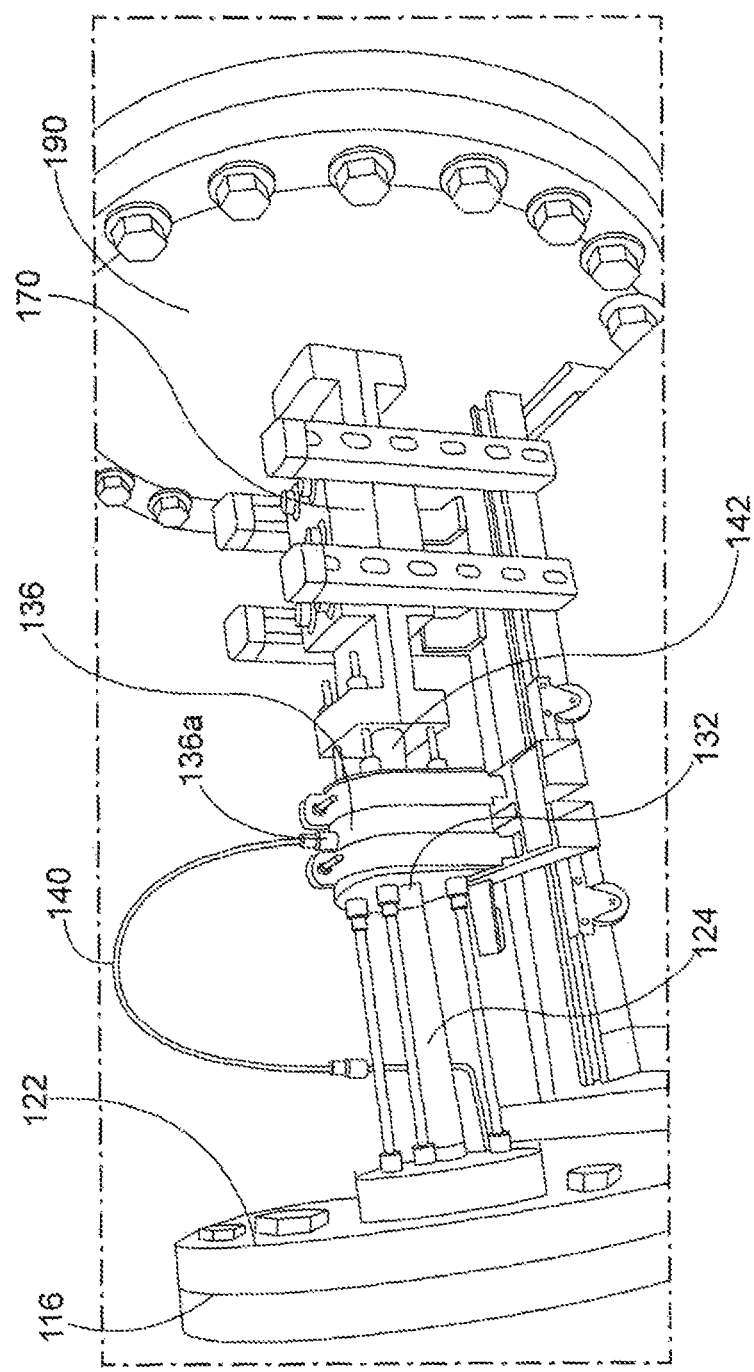
FIG. 4 shows a perspective view of an adapter block used in the gas accelerator shown in FIG. 1.
Figure 5:
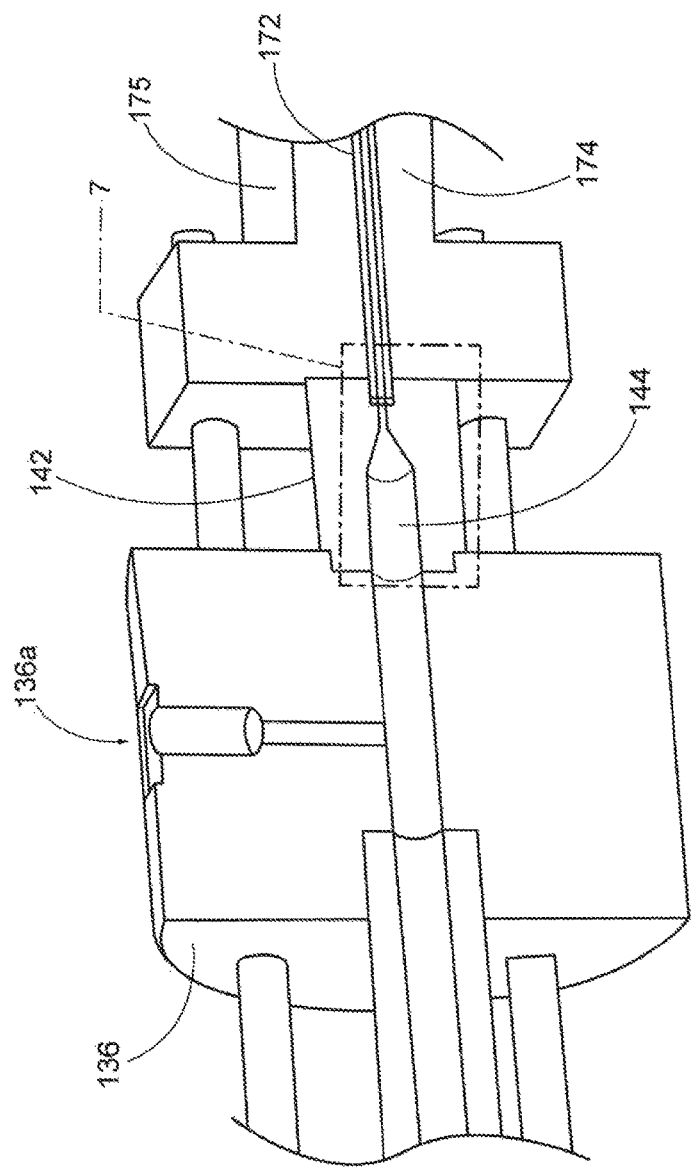
FIG. 5 shows a perspective view, in section, of the adapter block shown in FIG. 4.
Figure 6:
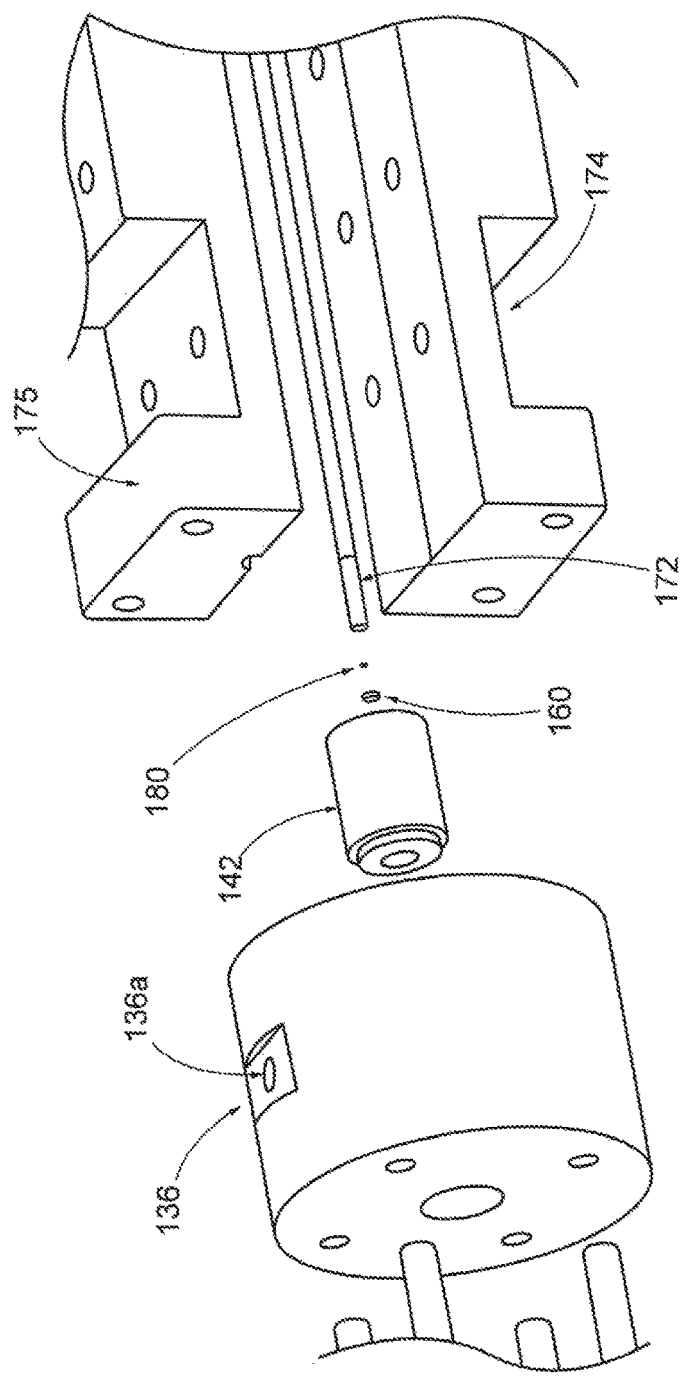
FIG. 6 shows an exploded perspective view, of a central portion of the gas accelerator shown in FIG. 1.

Discharge port 132 is removably attached to second stage 105, of which the first element is barrel fitting 136, shown in FIGS. 4-6. Barrel fitting 136 is releasably coupled to discharge end of barrel 124. Barrel fitting 136 includes a helium fill tap 136a that is connected to a vacuum and helium supply line 140 (shown in FIGS. 3A and 4). Vacuum and helium supply line 140 provides the ability to evacuate air out of the interior of barrel 124 and fill helium to the interior of barrel 124 downstream of piston 150 for compression by piston 150 during operation of accelerator 100. Helium is used due to its light weight, high speed of sound, and inertness, although those skilled in the art will recognize that other gases may be used. In an exemplary embodiment, the helium pressure may be about 4.35 psia (about 30 KPa absolute)

A receiver, or adapter block, 142 is releasably inserted into barrel fitting 136 and receives piston 150 from adapter block 142, which receives piston 150 from discharge port 132. A discharge end 143 of adapter block 142 ends in a conical, or tapered, cross-sectional cone 146, shown in FIG. 7. Tapered cone 146 includes a wider upstream diameter 148 that narrows to a narrower downstream end 149. Tapered cone 146 rapidly compresses the helium in barrel 124 that is trapped between discharge end 149 and piston 150 as piston 150 travels along barrel 124. Downstream end 149 is smaller in diameter than piston 150 so that piston 150 cannot travel forward of downstream end 149 and out of adapter block 142.

A frangible member in the form of a burst disc 160 is across downstream end 149 of tapered cone 146. In an exemplary embodiment, burst disc 160 is constructed from a polymer material, such as a polyester film, such as, for example, biaxially-oriented polyethylene terephthalate, sold commercially as "Mylar", although those skilled in the art will recognize that other suitable materials can be used. Burst disc 160 provides a barrier to prevent the escape of the helium from barrel 124 until a predetermined pressure is reached. The thickness and material, as well as scoring, of burst disc 160 are selected such that burst disc 160 bursts at a predetermined pressure of the helium gas as the helium gas is compressed forward of piston 150.

Referring back to FIG. 3, piston 150 includes a generally cylindrical body 152 with a forward o-ring 154 and a rear o-ring 156 that provide seals between body 152 and barrel 124 so that, as piston 150 travels along barrel 124, the helium gas forward of piston 150 is compressed between piston 150 and burst disc 160. As shown FIG. 3B, piston 150 is sufficiently long such that forward o-ring 154 is forward of air slots 130 and rear o-ring 156 is rearward of air slots 130 when piston 150 is inserted into barrel 154 and straddling air slots 130. In an exemplary embodiment, piston 150 has a bulbous nose 158. Those skilled in the art, however, will recognize that nose 158 of piston 150 can have other shapes, such as, for example, pointed, flat, or other shapes and can be made of various materials including the piston material or may be part of piston 150. Further, an exemplary piston 150 can weigh between approximately 8 grams and approximately 16 grams.

Figure 7:
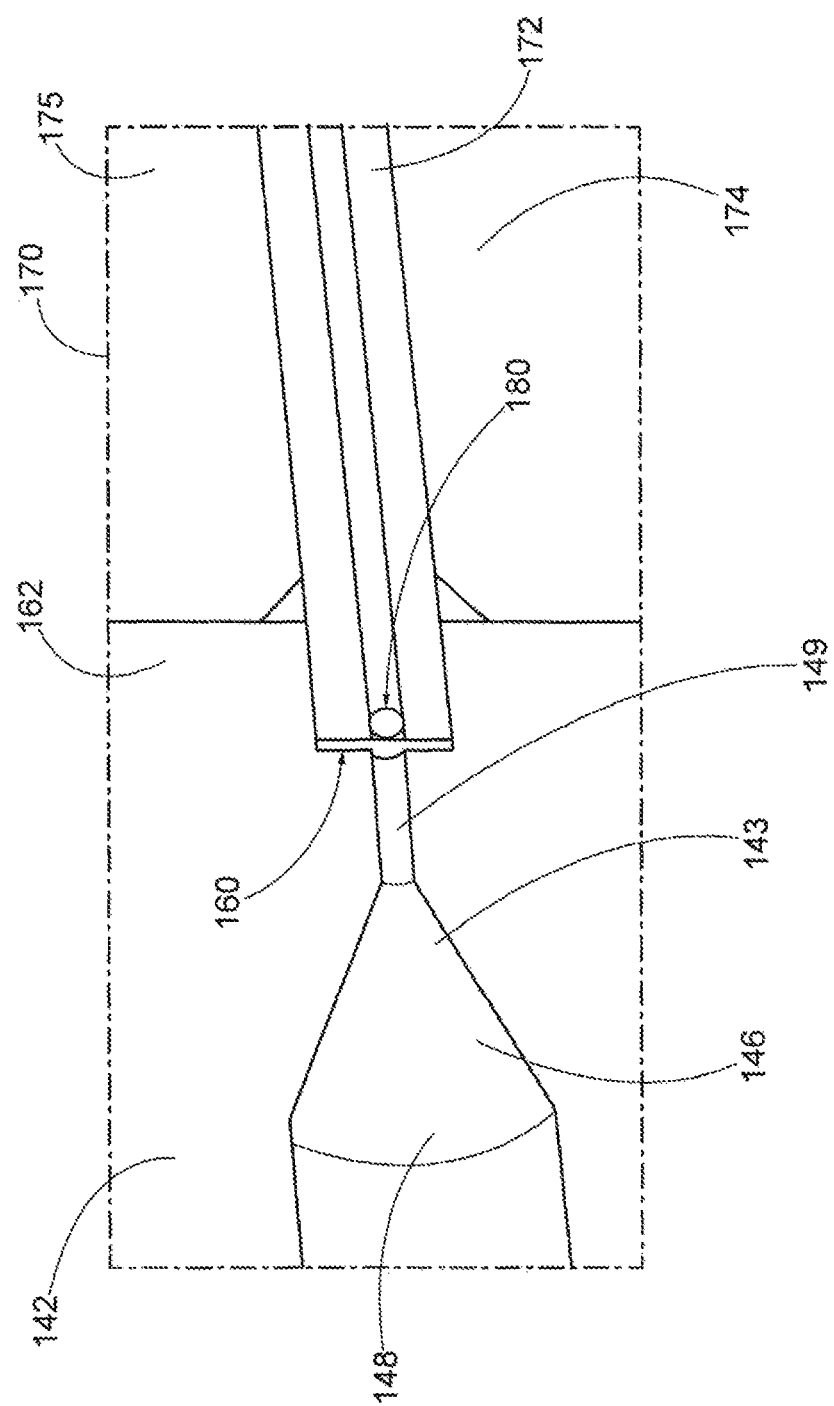
FIG. 7 shows a side elevational view, in section, of the central portion of the gas accelerator.

A forward end 162 of adapter block 142 is removably attached to flight tube assembly 170 which includes a flight tube 172 that is supported by a lower flight tube fitting 174 and an upper flight tube fitting 175, with flight tube 172 sandwiched therebetween. A projectile 180 is disposed in flight tube 172 and, as shown in FIG. 7, is seated against a downstream, or discharge, side of burst disc 160. An exemplary projectile 180 can be a nylon sphere having a diameter of about 1/16" (about 1.5 mm), although those skilled in the art will recognize that sphere 180 can be other sizes and/or shapes (e.g., a cylinder, a bullet, etc.) and be constructed form other materials. The rupture of burst disc 160 releases pressurized helium to the rear of burst disc 160 into flight tube 172 and accelerates projectile 180 to velocities of up to 5 kilometers per second along flight tube 172.

Figure 9:
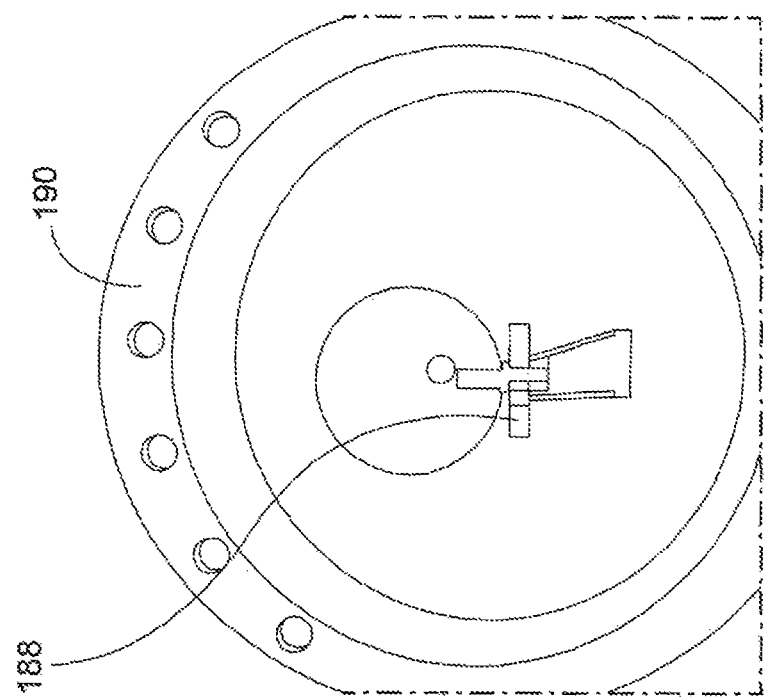
FIG. 9 shows the end view of FIG. 8, with the end cover removed.
Figure 8:
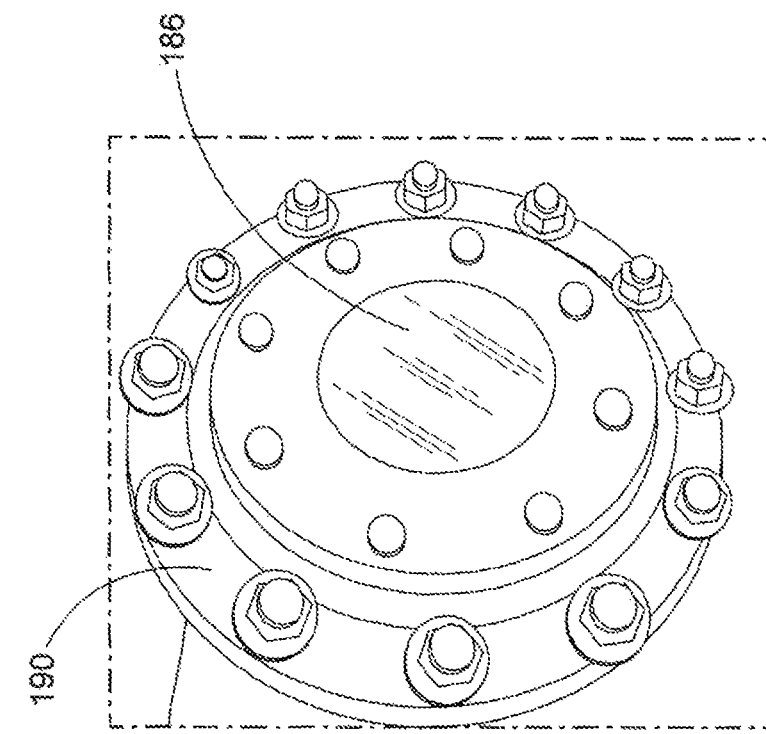
FIG. 8 shows a side view of a test chamber with observation port used in the gas accelerator shown FIG. 1.

A downstream end 176 of flight tube 172 discharges downstream into a target, or test, chamber 190, shown in FIGS. 1A and 8-9. An exemplary test chamber 190 is generally barrel shaped, with a length of about 1.3 meters and a width of about 1 meter. Test chamber 190 includes a plurality of ports 182, 184, 186 that can be used to access the interior of test chamber 190, such as, to add instrumentation 188, such as, for example, as shown FIG. 9. Instrumentation 188 can include optics to determine the speed of projectile 182, as well as targets (not shown) into which projectile 182 impacts after exiting flight tube 172 in order to determine the impact resistance of such targets. Further, test chamber 190 can be evacuated to a pressure of about 1 kPa absolute (about 0.145 psia).

Figure 10:
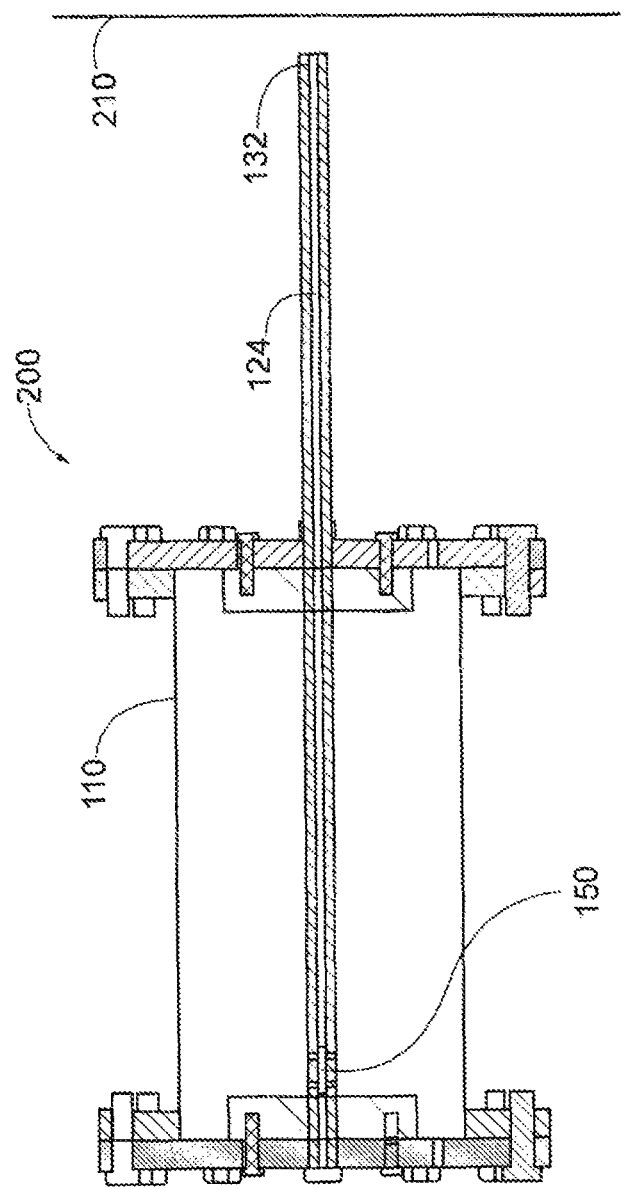
FIG. 10 shows a schematic view of a first alternative exemplary configuration of the gas accelerator according to the present invention.

Referring to FIG. 10, accelerator 100 can be modified to form an accelerator 200 by removing barrel fitting 136 and all components downstream of barrel fitting 136, leaving barrel 124 extending outwardly from compressed air chamber 110 and allowing piston 150 to be discharged from barrel 124 directly to a target 210. In this configuration, with a breech pressure of about 65 psig, piston 150 can be accelerated to a velocity of approximately 35 meters per second. Based on the weight of piston 150 of approximately 16 grams, target 210 can be impacted within energy of approximately 720 Joules.

Figure 11:
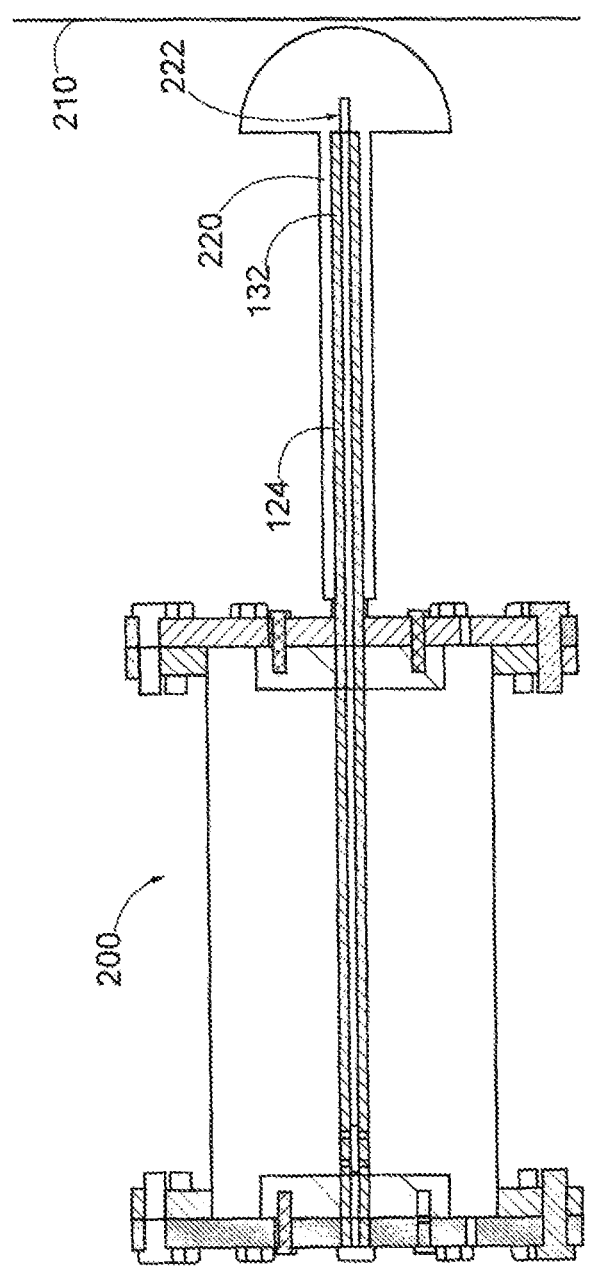
FIG. 11 shows a schematic view of a second alternative exemplary configuration of the gas accelerator according to the present invention.

Referring to FIG. 11, a large, slow speed projectile 220 can be slid over discharge port 132 of barrel 124 of accelerator 200. Upon operation of accelerated 200, piston 150 travels through barrel 124, impacting slow speed projectile 220, and launching slow speed projectile 220 from barrel 124 and against target 210. Optionally, slow speed projectile 220 can also include a piston pocket 222 that can receive and retain piston 150 upon impact of piston 150 with slow speed projectile 220, thereby stopping piston 150 from an uncontrolled discharge out of barrel 124. Piston pocket 222 also allows piston 150 to exit barrel 124, making a mechanical connection between the piston 150 and slow speed projectile 220, and allowing the air behind piston 150 to uniformly push the slow speed projectile 220 forward.

Slow speed projectile 220 can be used to simulate a relatively large, slower moving projectile, such as, for example, a soccer ball, while target 210 can simulate the head of a soccer player. Impact data of slow speed projectile 220 impacting target 210 can be used to help measure and determine concussive forces allowing for highly repeatable testing.

Figure 12:
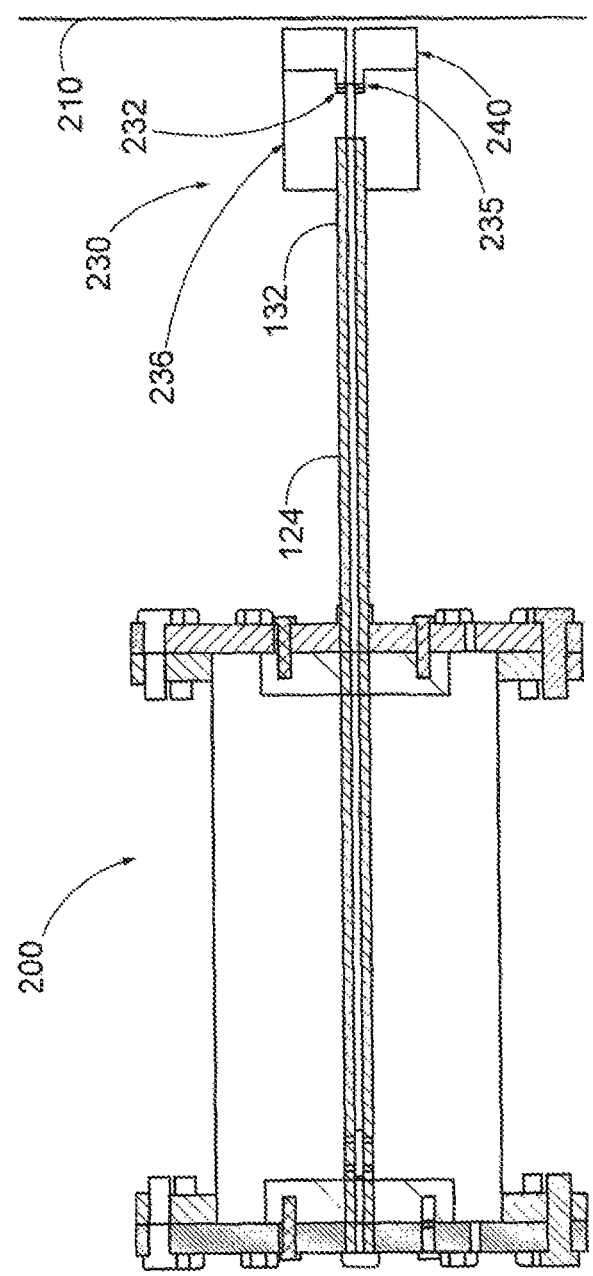
FIG. 12 shows a schematic view of a third alternative exemplary configuration of the gas accelerator according to the present invention.

Referring to FIG. 12, a sonic generator 230 can be slid over and secured to discharge port 132 of barrel 124 of accelerator 200. Sonic generator 230 includes an adapter block 236 that is disposed over discharge port 132 of barrel 124. Adapter block 236 retains a diaphragm 232. Optionally, a sacrificial washer 235 is disposed immediately downstream of diaphragm 232 and is used to catch piston 150 and prevent piston 150 from exiting barrel 124. A diaphragm compression holder 240 is disposed downstream of adapter block 236 and secures diaphragm 232 and sacrificial washer 236 within sonic generator 230.

As piston 150 traverses along barrel 124, piston 150 compresses any gas inside barrel 124 between piston 150 and diaphragm 232. When the gas pressure inside barrel 124 exceeds the burst pressure of diaphragm 232, diaphragm 232 ruptures, generating a shockwave that is directed against a target 210.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. A modular light gas accelerator comprising:
   a first stage including:
   a chamber having a rear portion and a discharge portion;
   a barrel located inside the chamber, the barrel having a rear port at the rear portion of the chamber and a discharge port extending outwardly from the discharge portion of the chamber; and
   a piston slidingly located inside the barrel proximate to the rear port and adapted to be propelled through the barrel and out of the discharge port;
   and
   a second stage removably attached to the discharge end of the first stage, the second stage including:
   a receiver adapted to receive the piston from the discharge port, the receiver having a receiver passage having a first upstream diameter and a second downstream diameter, smaller than the first upstream diameter;
   a frangible member extending across the second downstream diameter;
   a projectile located downstream of the frangible member, the projectile being adapted to travel along the receiver passage; and
   a target chamber located at a downstream end of the receiver passage, such that a target is able to be mounted in the target chamber and be struck by the projectile after the projectile exits the receiver passage.

2. The modular light gas accelerator according to claim 1, wherein the barrel comprises a sidewall, and wherein the sidewall has an opening therein, the opening being sized such that the piston is sufficiently large to obscure the entire opening.

3. The modular light gas accelerator according to claim 1, further comprising a vacuum line connection at the rear port.

4. The modular light gas accelerator according to claim 3, further comprising a spacer disposed in the barrel between the piston and the vacuum line connection.

5. The modular light gas accelerator according to claim 1, further comprising a port providing fluid communication to the chamber from exterior of the chamber.

6. The modular light gas accelerator according to claim 1, wherein the receiver passage has a conical cross section between the first upstream diameter and the second downstream diameter.

7. The modular light gas accelerator according to claim 1, further comprising a gas tap in fluid communication with the first upstream diameter.

8. The modular light gas accelerator according to claim 1, wherein the frangible member comprises a burst disc.

9. A modular light gas accelerator comprising:
   a launch portion comprising a compressed gas cylinder having an interior and a launch barrel located in the compressed gas cylinder, the barrel having an opening in fluid communication with the interior of the compressed gas cylinder, the opening having a length; and
   a target portion releasably connected to the launch portion, the target portion comprising:
   an adapter block having an input passage end in fluid communication with the barrel, an output passage end, and a passage having a decreasing diameter between the input passage end and the output passage end;
   a frangible member disposed downstream of the output passage end; and
   a projectile disposed downstream of the frangible member.

10. The modular light gas accelerator according to claim 9, wherein the launch portion further comprises an upstream port in fluid communication with the barrel.

11. The modular light gas accelerator according to claim 10, further comprising a piston movably disposed in the barrel, the piston having a length greater than the length of the opening.

12. The modular light gas accelerator according to claim 11, further comprising a spacer disposed between the upstream port and the piston such that, when the piston is in contact with the spacer, the piston occludes the opening.

13. The modular light gas accelerator according to claim 10, wherein the compressed gas cylinder is adapted to be connected to a compressed gas source.

14. The modular light gas accelerator according to claim 11, wherein the upstream port is adapted to be connected to the compressed gas source.

15. The modular light gas accelerator according to claim 9, wherein the adapter passage is conically shaped.

16. The modular light gas accelerator according to claim 9, further comprising a flight tube located downstream of the frangible member, wherein the projectile is slidably disposed in the flight tube.

17. A light gas accelerator comprising:
   a chamber having a rear portion and a discharge portion;
   a barrel located inside the chamber, the barrel having:
   a rear port at the rear portion of the chamber;
   a discharge port extending outwardly from the discharge portion of the chamber; and an opening proximate to the discharge end and in fluid communication with the chamber, the opening having a length; and a piston slidingly located inside the barrel proximate to the rear port and adapted to be propelled through the barrel and out of the discharge port, the piston having a length longer than the length of the opening.

18. The light gas accelerator according to claim 17, further comprising a projectile adapted to be slid over the barrel discharge port such that, upon the piston sliding along the barrel and exiting the discharge port, the piston encounters the projectile and pushes the projectile off of the barrel.

19. The light gas accelerator according to claim 17, further comprising a sonic generator adapted to be slid over the barrel discharge port such that, upon the piston sliding along the barrel and exiting the discharge port, the piston encounters the sonic generator, causing the sonic generator to emit a shock wave.

20. The light gas accelerator according to claim 17, further comprising a target chamber adapted to be connected to the barrel discharge port, the target chamber comprising a projectile such that the piston is propelled along the barrel to the barrel discharge port at a piston speed and, after the piston exits the barrel discharge port, the projectile is propelled at a speed higher than the piston speed.

* * * * *